United States Patent
Kang et al.

(10) Patent No.: US 10,063,806 B2
(45) Date of Patent: Aug. 28, 2018

(54) ENDOSCOPY SYSTEM AND METHOD FOR PROCESSING IMAGE OF THE SAME

(71) Applicant: INTHESMART Inc., Seoul (KR)

(72) Inventors: Uk Kang, Seoul (KR); Ilhyung Shin, Jeju (KR)

(73) Assignee: INTHESMART INC., Seoul (KR)

( * ) Notice: Subject to any disclaimer, the term of this patent is extended or adjusted under 35 U.S.C. 154(b) by 290 days.

(21) Appl. No.: 15/143,927

(22) Filed: May 2, 2016

(65) Prior Publication Data

US 2016/0381263 A1    Dec. 29, 2016

(30) Foreign Application Priority Data

Jun. 26, 2015  (KR) .................. 10-2015-0090836

(51) Int. Cl.
| H04N 5/225 | (2006.01) |
| H04N 7/00 | (2011.01) |
| A61B 1/00 | (2006.01) |

(52) U.S. Cl.
CPC ......... *H04N 7/002* (2013.01); *A61B 1/00009* (2013.01); *H04N 2005/2255* (2013.01)

(58) Field of Classification Search
CPC ............................. H04N 7/002; A61B 1/00009
USPC ........................................................ 348/68
See application file for complete search history.

(56) References Cited

U.S. PATENT DOCUMENTS

| 2010/0063352 | A1* | 3/2010 | Matsuura | ............. A61B 1/0638 600/103 |
| 2010/0274090 | A1* | 10/2010 | Ozaki | ............... A61B 1/00096 600/173 |
| 2012/0016202 | A1* | 1/2012 | Baum | ............... A61B 1/00114 600/182 |
| 2014/0018668 | A1* | 1/2014 | Zheng | ................. A61B 8/4254 600/424 |
| 2014/0320618 | A1* | 10/2014 | Akahane | ............... H04N 5/363 348/65 |

FOREIGN PATENT DOCUMENTS

KR    10-2007-0071556 A    7/2007

* cited by examiner

*Primary Examiner* — Nguyen Truong
(74) *Attorney, Agent, or Firm* — Patent Office of Dr. Chung Park

(57) ABSTRACT

Provided is an endoscopy system including: an image signal generating unit which is connected to one side of a cable, and which includes a signal transmission unit configured to convert an image signal of inner body according to a protocol for long distance transmission and transmit a converted image signal so as to achieve transmission of the image signal through the cable; a signal processing unit connected to the other side of the cable, and receiving the converted image signal transmitted through the cable and converting the converted image signal into the image signal; a CPU configured to output a user interface for the image signal and an operation control signal according to a handling of the user interface of user; an image processing unit configured to overlap the user interface on the image signal output from the signal processing unit and process the image signal according to the operation control signal.

13 Claims, 6 Drawing Sheets

ENDOSCOPY SYSTEM AND METHOD FOR PROCESSING IMAGE OF THE SAME

CROSS-REFERENCE TO RELATED APPLICATIONS

This application claims priority under 35 U.S.C. § 119 from Korean Application No. 10-2015-0090836 filed on Jun. 26, 2015, the subject matter of which is incorporated herein by reference.

BACKGROUND OF THE INVENTION

Field of the Invention

The present disclosure relates to an endoscopy system and a method for processing an image of the endoscopy system.

Description of the Related Art

Since an endoscopy system provides a doctor with an image of the inner body in a surgery or checkup procedure and the doctor can check the image, it is possible to accurately and reliably accomplish the surgery or the checkup procedure.

Recently, the endoscopy system is increasingly required to provide various functions as well as just images.

Accordingly, a research on an endoscopy system that can provide various functions while performing a high speed image processing is progressed.

SUMMARY OF THE INVENTION

The present disclosure has been made in view of the above problems, and provides an endoscopy system and a method for processing an image of the endoscopy system capable of providing various functions while performing a high speed image processing.

The present disclosure further provides an endoscopy system and a method for processing an image of the endoscopy system capable of providing a high-speed processing of an image signal by processing the image signal and an additional image signal.

In accordance with an aspect of the present disclosure, an endoscopy system includes: an image signal generating unit which is connected to one side of a cable, and which includes a signal transmission unit configured to convert an image signal of inner body according to a protocol for long distance transmission and transmit a converted image signal so as to achieve transmission of the image signal through the cable; a signal processing unit 200 which is connected to the other side of the cable, and which receives the converted image signal transmitted through the cable and converts the converted image signal into the image signal; a CPU configured to output a user interface for the image signal and an operation control signal according to a handling of the user interface of user; and an image processing unit configured to overlap the user interface on the image signal output from the signal processing unit and process the image signal according to the operation control signal.

The endoscopy system further includes a monitoring unit that monitors at least one of the signal processing unit, the CPU, and the image processing unit in real time to perform at least one reset according to at least one state value.

When the CPU performs an image processing for the image signal, an image processing speed for the image signal by the image processing unit is faster than the image processing speed by the CPU.

The CPU matches a disease display image data of a database or a local table with the image signal, and a matched result is overlapped on the image signal processed by the image processing unit.

The CPU outputs a processing control signal for selecting at least one of a plurality of filters of the image processing unit, and the filter selected according to the processing control signal processes the image signal at a high speed in comparison with the image processing speed of the CPU.

The monitoring unit receives an operation control signal or a processing control signal for controlling transmission or conversion of the image signal from the CPU, and transmits a control command corresponding to the operation control signal or the processing control signal to at least one of the signal transmission unit, the signal processing unit, and the image processing unit.

In accordance with another aspect of the present disclosure, an endoscopy system includes: an image signal generating unit which is connected to one side of a cable, and which is configured to convert an image signal of inner body having n frames per second and an additional image signal of inner body having m frames per second into a converted image signal according to a protocol for long distance transmission so that it is possible to transmit the image signal and the additional image signal via the cable; a signal processing unit which is connected to the other side of the cable, and which is configured to convert the converted image signal transmitted through the cable into the image signal and the additional image signal, and to transmit the image signal and the additional image signal to a first transmission path and a second transmission path respectively; a CPU configured to transmit the additional image signal transmitted via the second transmission path at a speed lower than a transmission speed of the image signal in the first transmission path; and an image processing unit configured to overlap the image signal transmitted through the first transmission path and the additional image signal output from the CPU.

The image signal generating unit includes: an image sensing unit configured to generate the image signal; an additional image sensing unit configured to generate the additional image signal; a serializer configured to integrate the image signal and the additional image signal to generate a serial signal; and a signal transmission unit which is connected to one side of the cable, and which is configured to convert and transmit the serial signal into the converted image signal according to the protocol for long distance transmission so as to transmit the serial signal via the cable.

The signal processing unit includes: a signal reception unit which is connected to the other side of the cable, and which is configured to receive the converted image signal via the cable to convert into the serial signal; a deserializer configured to divide the serial signal into the image signal and the additional image signal; and a path forming unit configured to output the image signal to the first transmission path, and output the additional image signal to the second transmission path.

The endoscopy system further includes a monitoring unit that monitors at least one of the signal processing unit, the CPU, and the image processing unit in real time to perform at least one reset according to at least one state value.

A transmission speed of the image signal in the first transmission path is faster than a transmission speed of the additional image signal in the second transmission path.

A bandwidth of the image signal in the first transmission path is wider than a bandwidth of the additional image signal in the second transmission path.

When the CPU performs an image processing for the image signal, an image processing speed for the image signal by the image processing unit is faster than the image processing speed by the CPU.

The endoscopy system further includes a light emitting unit that irradiates a light to the inner body, wherein the image signal generating unit comprises an image sensing unit that generates the image signal, and, when an amount of the radiated light exceeds an amount of light that can be accepted by the image sensing unit, the CPU controls the light emitting unit to reduce an intensity of light.

The image signal generating unit further includes a first conversion unit that converts the converted image signal into an analog signal to transmit to one side of the cable, and the signal processing unit further includes a second conversion unit that converts the analog signal transmitted via the other side of the cable into the converted image signal of a digital signal type.

The cable is a coaxial cable or a twisted cable.

The CPU outputs a user interface for at least one of the image signal and the additional image signal, and outputs an operation control signal according to a user interface handling of a user, and the image processing unit overlaps the user interface together with the image signal and the additional image signal and processes at least one of the image signal and the additional image signal according to the operation control signal.

The monitoring unit receives an operation control signal or a processing control signal for controlling transmission or conversion of the image signal from the CPU, and transmits a control command corresponding to the operation control signal or the processing control signal to at least one of the signal transmission unit, the signal processing unit, and the image processing unit.

The image sensing unit generates the image signal of n frames per second, the additional image sensor generates the additional image signal of m frames per second, and the m is smaller than the n.

In accordance with another aspect of the present disclosure, a method for processing an image of an endoscopy system includes: converting an image signal of inner body according to a protocol for long distance transmission and transmitting a converted image signal so as to achieve transmission of the image signal through a cable of an endoscope; receiving the converted image signal transmitted through the cable and converting the converted image signal into the image signal; outputting a user interface for the image signal and an operation control signal according to a handling of the user interface of a user; and overlapping the user interface on the image signal and processing the image signal according to the operation control signal.

BRIEF DESCRIPTION OF THE DRAWINGS

The objects, features and advantages of the present disclosure will be more apparent from the following detailed description in conjunction with the accompanying drawings, in which.

DETAILED DESCRIPTION OF EXEMPLARY EMBODIMENTS

Exemplary embodiments of the present disclosure are described with reference to the accompanying drawings in detail. The terms and words used in the following description and claims are not limited to the bibliographical meanings, but, are merely used by the inventor to enable a clear and consistent understanding of the present disclosure. It is to be understood that the singular forms "a," "an," and "the" include plural referents unless the context clearly dictates otherwise.

In the present disclosure, the terms such as "include" and/or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

An endoscopy system according to a first embodiment and a second embodiment of the present disclosure is described with reference to the accompanying drawings.

Figure 1:
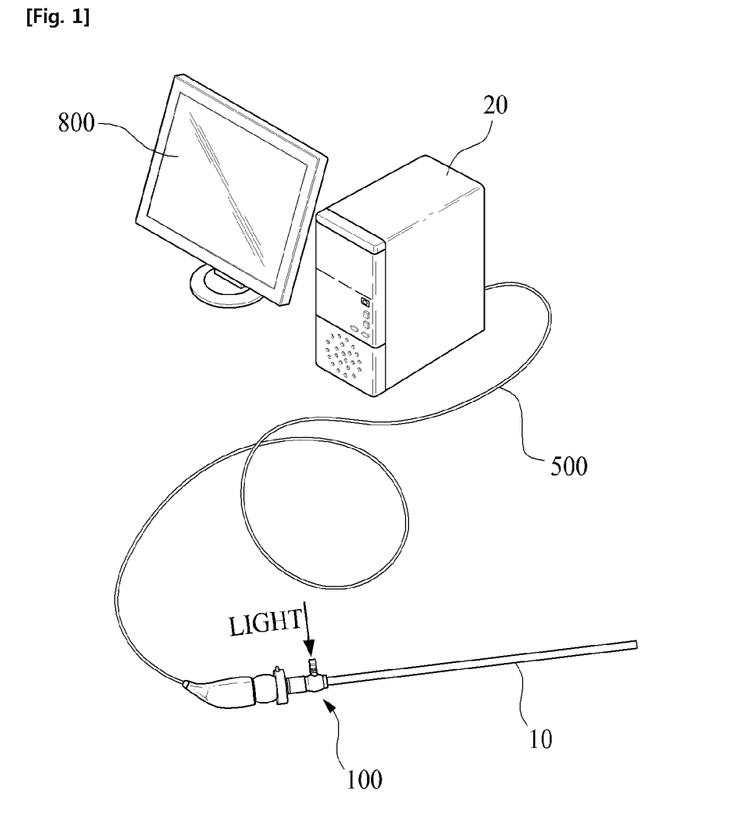
FIG. 1 is a diagram illustrating a configuration of an endoscopy system according to a first embodiment and a second embodiment of the present disclosure.

FIG. 1 is a diagram illustrating a configuration of an endoscopy system according to a first embodiment and a second embodiment of the present disclosure. As shown in FIG. 1, the configuration illustrated in FIG. 1 may include an image signal generating unit 100 which is connected to one end of a cable 500 of the endoscopy system according to the first embodiment and the second embodiment of the present disclosure.

The image signal generating unit 100 may include an image sensing unit (not shown) or an additional image sensing unit (not shown). The image sensing unit and the additional image sensing unit are described in detail later.

The image signal generating unit 100 may be coupled to a telescope 10 having a lens array contained therein. A light guiding unit for inducing light of a light emitting unit to the image sensing unit or the additional image sensing unit may be provided in the inside of the telescope 10.

A body 20 may be connected to the other end of the cable 500, and may be equipped with at least one constituent element of hardware or software that processes an image signal or an additional image signal. The image signal and the additional image signal are described in detail later with reference to the drawing.

The configuration illustrated in FIG. 1 is just an example of a configuration of the endoscopy system according to the first embodiment and the second embodiment of the present disclosure, but it is not limited thereto.

Figure 2:
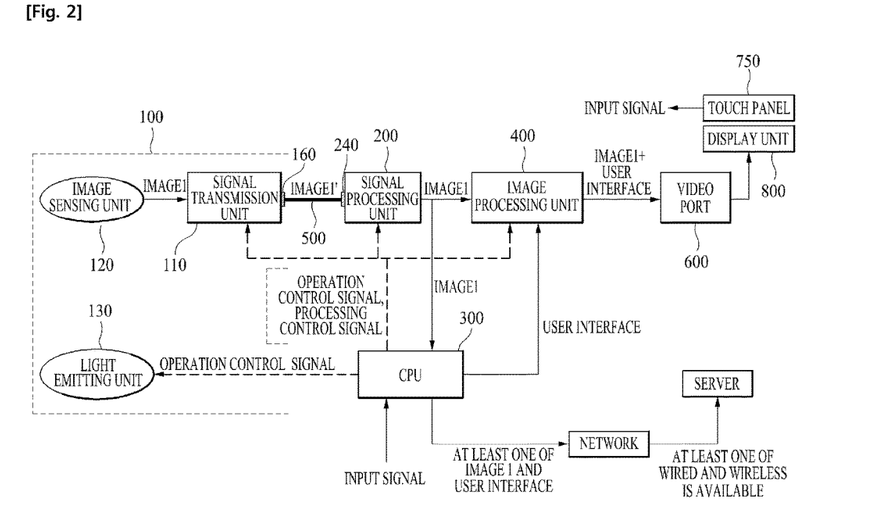
FIG. 2 and FIG. 3 are a block diagram illustrating an endoscopy system according to a first embodiment of the present disclosure.
Figure 3:
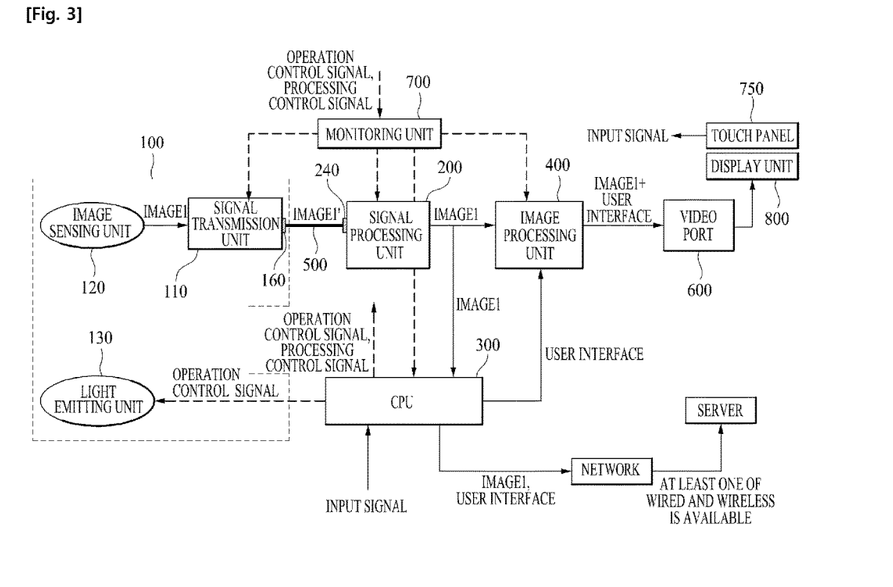

FIG. 2 and FIG. 3 are a block diagram illustrating an endoscopy system according to a first embodiment of the present disclosure. The block diagram of an endoscopy system according to a second embodiment of the present disclosure is described in detail later with reference to FIG. 4 and FIG. 5.

As shown in FIG. 2, the endoscopy system according to a first embodiment of the present disclosure may include the image signal generating unit 100, a signal processing unit 200, CPU 300, and an image processing unit 400.

The image signal generating unit 100 may be connected to one side of the cable 500, and may include a signal transmission unit 110 configured to convert an image signal (IMAGE 1) according to a protocol for long distance transmission and transmit a converted image signal (IMAGE 1') so as to achieve the transmission of the image signal (IMAGE 1) of the inner body through the cable 500.

At this time, the image signal generating unit 100 may include an image sensing unit 120 for generating the image signal (IMAGE 1), and the image sensing unit 120 may include a CCD device or a CMOS device.

In addition, the image signal generating unit 100 may include a light emitting unit 130 that emits light when the image signal generating unit 100 is inserted into the inner body. Such a light emitting unit 130 may include an LED, and the intensity of radiation may be adjusted under the control of CPU 300.

The signal transmission unit 110 may convert the image signal (IMAGE 1) by using a universal serial bus (USB) protocol so as to transmit the image signal (IMAGE 1) to the cable 500 of about several meters, but the protocol for long distance transmission is not limited to the USB protocol.

The endoscopy system should display the image of the internal body quickly and accurately through a display unit 800 to be helpful in the surgery or the checkup procedure by a doctor, which is described in more detail later.

Therefore, it can be seen that when the time that takes from the generation of the image signal (IMAGE 1) by the image sensing unit 120 to the display of the image signal through the display unit 800 is shorter, the performance of the endoscopy system is better. The length of the cable 500 included in the endoscopy system may be about several meters, and such a length of the cable 500 may be considered as a long distance from the image processing point of view of the endoscopy system.

When the image signal (IMAGE 1) is transmitted via the cable 500 of about several meters, the image may not be displayed quickly and accurately on the display unit 800 due to the omission or modification of the image signal.

To prevent this, the endoscopy system according to an embodiment of the present disclosure can quickly and accurately display the image of the inner body by converting the image signal (IMAGE 1) into a converted image signal (IMAGE 1') according to the protocol for long distance transmission.

Meanwhile, the signal processing unit 200 may be connected to the other side of the cable 500, and may receive the converted image signal (IMAGE 1') transmitted through the cable 500 to convert into the image signal (IMAGE 1).

CPU 300 may output a user interface for the image signal (IMAGE 1) and an operation control signal according to the handling of the user interface of user. The user interface may include a menu, and may be used for the operation control of the endoscopy system and the handling of the image displayed on the display unit 800. The operation of the image through the user interface may be intended for the enlargement or the reduction of an image, a sharpness or a luminance change, or the like, but it is not limited thereto.

At this time, although not shown in the drawings, CPU 300 may include memory (not shown) for storing data for the user interface.

The image processing unit 400 may overlap the user interface on the image signal (IMAGE 1) output from the signal processing unit 200 and process the image signal (IMAGE 1) according to the operation control signal.

In this case, at least one of the signal transmission unit 110, the signal processing unit 200 and the image processing unit 400 may be implemented of a field-programmable gate array (FPGA), but it is not limited thereto.

The FPGA is one of programmable non-memory semiconductors, and the circuit of the FPGA can be changed again for a particular use, unlike a normal semiconductor which is impossible to change the circuit for a particular use. A desired circuit of the FPGA may be implemented through the operation of a switching device which is a hardware element, so that it is impossible to process or transmit the image signal (IMAGE 1) at a high speed in comparison with the case where the image signal (IMAGE 1) is transmitted or processed by software.

The image processing unit 400 may transmit the overlapped image signal and the user interface to the display unit 800 via a video port 600. The video port 600 may be an image graphics array (VGA), a digital visual interface (DVI), a high definition multimedia interface (HDMI), or a low voltage differential signaling (LVDS), but it is not limited thereto.

In the endoscopy system according to the first embodiment of the present disclosure, the processing path of the user interface may be different from the processing path of the image signal (IMAGE 1). That is, in the case of the endoscopy system according to the first embodiment of the present disclosure, CPU 300 may process the user interface, and the signal transmission unit 110, the signal processing unit 200, and the image processing unit 400 may process the image signal (IMAGE 1).

A doctor may perform a surgery on a patient while viewing the image generated by the endoscopy system, and it is possible to perform an accurate surgery only when the doctor is able to see the conditions of the inner body immediately through an image.

If the doctor is not able to see the image of the inner body immediately in the surgical procedure, when the doctor makes a mistake accidentally, the doctor may not immediately recognize the mistake.

Therefore, the endoscopy system should be able to process the image signal (IMAGE 1) of the inner body at a high speed to display on the display unit 800 such as a monitor. On the other hand, even when the processing of the user interface is delayed, it may not have a significant impact on the surgical procedure, in comparison with the image processing of the image signal (IMAGE 1) of the inner body.

Unlike the endoscopy system according to the first embodiment of the present disclosure, when the image signal and the user interface are processed through a single image processing path, the processing of the image signal may be delayed due to the processing of the user interface, which may affect the surgery.

In the endoscopy system according to the first embodiment of the present disclosure, the signal transmission unit 110, the signal processing unit 200, and the image processing unit 400 may process the image signal (IMAGE 1) at a high speed and CPU 300 may process the user interface at a relatively low speed such that the image processing unit 400 may overlap the image signal (IMAGE 1) and the user interface.

Accordingly, since the doctor is able to see the overlapped image signal (IMAGE 1) and the user interface through the display unit 800, the doctor may utilize various functions of the endoscopy system through the handling of the user interface while feeling less or not being aware of the time delay generated according to the processing of the image signal (IMAGE 1).

Meanwhile, as shown in FIG. 3, the endoscopy system according to the first embodiment of the present disclosure may further include a monitoring unit 700. The monitoring unit 700 may monitor at least one of the signal processing unit 200, CPU 300, and the image processing unit 400 in real time. In this case, the monitoring unit 700 may perform at least one reset according to at least one state value.

Since the endoscopy system is used for a medical use, the processing of the image signal (IMAGE 1) should always be stable. For example, if a doctor cannot see the image of the inner body during a surgical procedure, the surgical procedure may not be accomplished smoothly.

Therefore, the monitoring unit 700 may perform a real-time monitoring of at least one of the signal processing unit 200, the image processing unit 400, and CPU 300 that perform the processing of the image and the user interface. For example, the monitoring unit 700 may receive the state value of at least one of the signal processing unit 200, the image processing unit 400, and CPU 300 every 1 ms, but a cycle of receiving the state value may be longer or shorter than 1 ms.

The monitoring unit 700 may reduce or minimize an abnormal image processing or a user interface processing time by resetting a corresponding constituent element of the state value indicating abnormality or error.

In addition, the monitoring unit 700 may reset the signal transmission unit 110 according to the state value of the signal transmission unit 110 that transmits the image signal (IMAGE 1).

Since the monitoring unit 700 performs a simple function in comparison with CPU 300, it may be implemented in the form of a micro control unit or a firmware.

Meanwhile, c.

In this case, the control command of the monitoring unit 700 may be identical with to the operation control signal or the processing control signal output from CPU 300, and may be a signal which is converted, by the monitoring unit 700, to be adjusted to at least one of the signal transmission unit 110, the signal processing unit 200, and the image processing unit 400.

At this time, the processing control signal may be used to control the transmission, the conversion, and the image overlapping of the image signal (IMAGE 1) which are accomplished in at least one of the signal transmission unit 110, the signal processing unit 200, and the image processing unit 400, but it is not limited thereto.

As described above, CPU 300 cannot check the current state (e.g., failure, abnormal operation or normal operation, and the like) of at least one of the signal transmission unit 110, the signal processing unit 200, and the image processing unit 400 in real time, but the monitoring unit 700 may check the at least one of the signal transmission unit 110, the signal processing unit 200, and the image processing unit 400 in real time.

Therefore, CPU 300 may transmit the operation control signal or the processing control signal to the monitoring unit 700, and the monitoring unit 700 may transmit a control command corresponding to the operation control signal or the processing control signal to the at least one of the signal transmission unit 110, the signal processing unit 200, and the image processing unit 400 in real time.

When the at least one constituent element performs failure or malfunction, even if CPU 300 transmits the operation control signal or the processing control signal, the monitoring unit 700 may reset the constituent element that performs failure or malfunction and notify this to CPU 300, so that CPU 300 may perform an operation corresponding to the failure or malfunction of the constituent element.

That is, the endoscopy system according to the first embodiment of the present disclosure of FIG. 2 does not include the monitoring unit 700, and CPU 300 may transmit the operation control signal or the processing control signal to the at least one of the signal transmission unit 110, the signal processing unit 200, and the image processing unit 400.

Since CPU 300 controls an overall operation of the endoscopy system, the amount of calculation processing is large. Thus, there is a limit on the real-time monitoring of the signal transmission unit 110, the signal processing unit 200, and the image processing unit 400. However, since the endoscopy system of FIG. 3 may determine the operation state in real time through a separate monitoring unit 700 independent of CPU 300, an operation stability of the endoscopy system may be significantly increased.

Meanwhile, as shown in FIG. 2 and FIG. 3, when CPU 300 performs the image processing for the image signal (IMAGE 1), an image processing speed for the image signal (IMAGE 1) by the image processing unit 400 may be faster than an image processing speed by CPU 300.

CPU 300 as well as the image processing unit 400 may perform the image processing for the image signal (IMAGE 1). At this time, since CPU 300 should perform the image processing having a large amount of calculation, and the image processing unit 400 should perform the image processing at a high speed, the image processing unit 400 may perform a simple image processing in comparison with the image processing of CPU 300.

For example, CPU 300 may perform a pattern matching with respect to a database (not shown) or a disease indicating image data of a local table (not shown) and the image signal (IMAGE 1), and the matched result may be overlapped in the image signal (IMAGE 1) processed by the image processing unit 400.

In this case, the database or the local table may be stored in a memory provided in CPU 300, or may be stored in a remote memory device which can be connected via a network.

The image of various diseases of the inner body may be previously stored in the database or the local table. At this time, when the endoscopy system according to the first embodiment of the present disclosure generates an image signal (IMAGE 1) containing an image of a specific disease, CPU 300 may select an image similar to the image signal (IMAGE 1) by comparing the image signal (IMAGE 1) with the image previously stored in the database or the local table.

Since such an operation of CPU should process a large amount of calculation such as the comparison between the image signal (IMAGE 1) and the feature point of the pre-stored image or the edge detection, the processing speed may be decreased.

In addition, CPU 300 may the output processing control signal for selecting at least one of a plurality of filters of the image processing unit 400, and the filter selected according to the processing control signal may process the image signal (IMAGE 1) at a high speed in comparison with the image processing speed of CPU 300.

At this time, CPU 300 of FIG. 2 may output a processing control signal for filter selection to the image processing unit 400. In addition, CPU 300 of FIG. 3 may output the processing control signal for filter selection to the monitoring unit 700, and the monitoring unit 700 may output a control command corresponding to the processing control signal for filter selection to the image processing unit 400.

The image processing unit 400 may include a plurality of filters such as a sharpening filter or a reflected light control filter, and may perform pre-processing for the image signal through the selected filter. Since the image pre-processing using a filter does not have a large calculation amount, the image processing unit 400 is able to perform a high-speed image processing.

Accordingly, in the case of the endoscopy system according to the first embodiment of the present disclosure, a time when the image signal (IMAGE 1) generated by the image sensing unit 120 is displayed through the display unit 800 may be within 100 ms, and preferably, may be within 30 ms.

If the time is within 100 ms, a doctor does not significantly recognize a time delay due to the image processing, and such a time delay may not be so serious and may not affect a surgery or checkup procedure. In addition, if the time is within 30 ms, the doctor hardly feel the time delay caused by the image processing, such that the surgery or the checkup procedure can be accomplished smoothly.

Meanwhile, the endoscopy system according to the first embodiment of the present disclosure may further include an input unit 750 by which a user can handle the user interface. The input unit 750 according to the first embodiment of the present disclosure may be a touch panel installed on the display unit 800, but it is not limited thereto. For example, the input unit 750 may be a keyboard, a mouse or a stylus.

When the user handles the input unit 750 to use the user interface, the input unit 750 may output an input signal corresponding to a user's handling to CPU 300. Accordingly, CPU 300 may perform an operation according to the input signal.

Meanwhile, the image signal generating unit 100 may further include a first conversion unit 160 which converts a converted image signal (IMAGE 1') into an analog signal to transmit to one side of the cable 500. In addition, the signal processing unit 200 may further include a second conversion unit 240 which converts the analog signal transmitted via the other side of the cable 500 into a converted image signal (IMAGE 1') of a digital signal type.

The first conversion unit 160 may include a phy chip connected to one side of the cable 500, and the second conversion unit 240 may include a dephy chip connected to the other side of the cable 500.

The pie chip may convert the converted image signal (IMAGE 1') of a digital signal type into an analog signal, and the dephy chip may convert the analog signal into a converted image signal (IMAGE 1') of a digital signal type.

Unlike the first embodiment of the present disclosure, when a square wave digital signal cable 500 is transmitted to a distance at a high-speed of several Gbps to the signal processing unit 200 via the cable 500, an edge of the square wave may be distorted. To prevent this, the endoscopy system according to the first embodiment of the present disclosure may convert the converted image signal (IMAGE 1') of a digital signal type into an analog signal so that it is possible to transmit the converted image signal (IMAGE 1') to a distance at a high-speed.

Next, an endoscopy system according to a second embodiment of the present disclosure is described with reference to the drawings.

Figure 4:
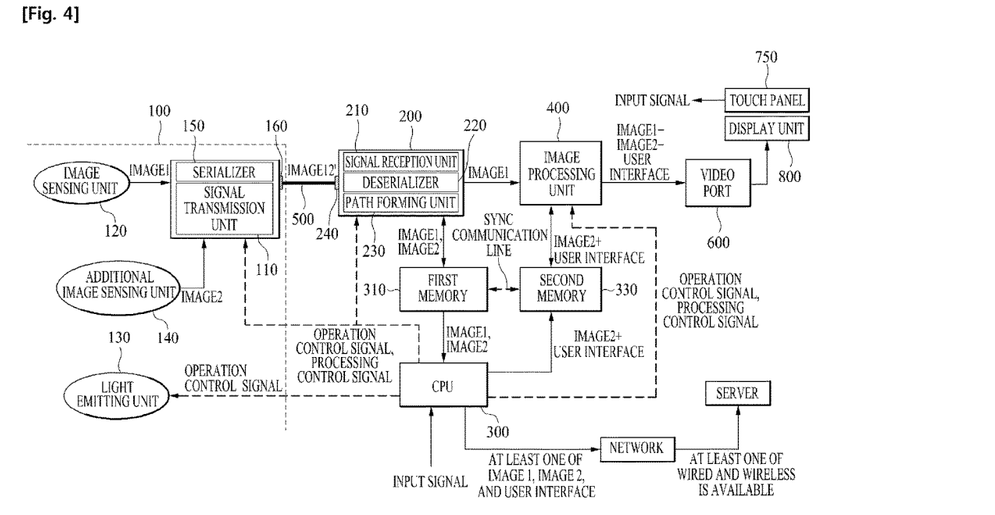
FIG. 4 and FIG. 5 is a block diagram illustrating an endoscopy system according to a second embodiment of the present disclosure.
Figure 5:
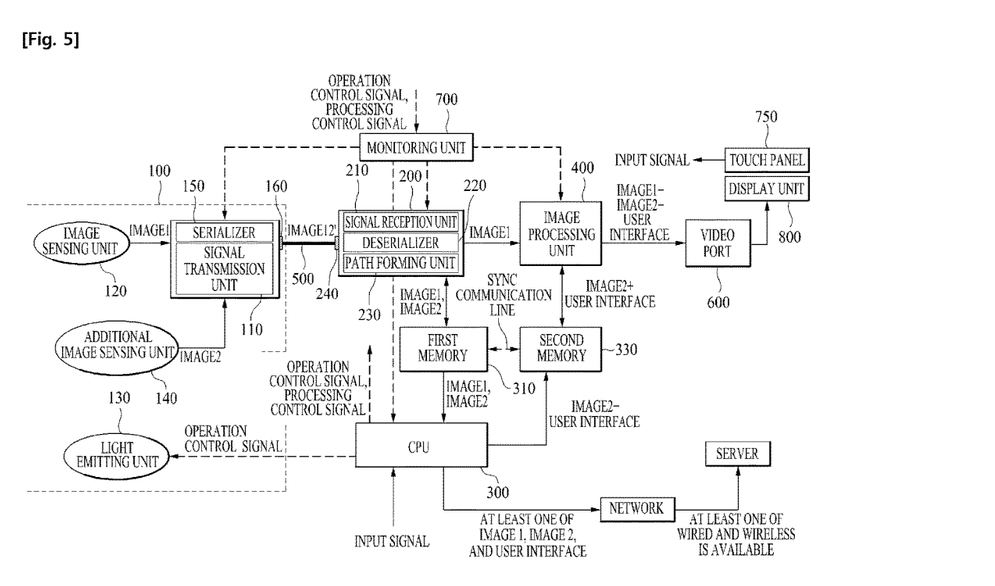

As shown in FIG. 4 and FIG. 5, the endoscopy system according to the second embodiment of the present disclosure may include the image signal generating unit 100, the signal processing unit 200, CPU 300, and the image processing unit 400.

The image signal generating unit 100 may be connected to one side of the cable 500. In addition, the image signal generating unit 100 may convert an image signal (IMAGE 1) of inner body having n frames per second and an additional image signal (IMAGE 2) of inner body having m frames per second into a converted image signal (IMAGE 12') according to the protocol for long distance transmission so that it is possible to transmit the image signal (IMAGE 1) and the additional image signal (IMAGE 2) via the cable 500.

The additional image signal (IMAGE 2) may be an image for each wavelength band (e.g., near infrared, infrared, ultraviolet, etc.) excluding a visible light or an image for a fluorescent material used in the fluorescence endoscopy or the fluorescence endoscopy surgery, and may be an image for specific target such as a lesion.

Since the protocol for long distance transmission is described in detail through the above first embodiment, a description thereof is omitted.

The signal processing unit 200 may be connected to the other side of the cable 500. In addition, the signal processing unit 200 may convert the converted image signal (IMAGE 12') transmitted through the cable 500 into the image signal (IMAGE 1) and the additional image signal (IMAGE 2). The signal processing unit 200 may transmit the image signal (IMAGE 1) to a first transmission path, and transmit the additional image signal (IMAGE 2) to a second transmission path. At this time, the signal processing unit 200 may also transmit the image signal (IMAGE 1) to the second transmission path.

CPU 300 may transmit the additional image signal (IMAGE 2) transmitted via the second transmission path at a speed lower than a transmission speed of the image signal (IMAGE 1) in the first transmission path. The image processing unit 400 may overlap the image signal (IMAGE 1) transmitted through the first transmission path and the additional image signal (IMAGE 2) output from CPU 300. Accordingly, the image signal (IMAGE 1) may be a background image, and the display unit 800 may display the additional image images (IMAGE 2) superimposed on the background image.

As described above, the image signal may be processed at a high speed in comparison with the additional image signal (IMAGE 2) (IMAGE 1). Since the image signal (IMAGE 1) indicates the state of the inner body, if the time delay from a time when the generation of the image signal (IMAGE 1) to a time when the generated image signal is displayed on the display unit 800 is short, accurate information may be provided to a doctor.

Since the additional image signal (IMAGE 2) may be an image for a fluorescent material or an image for each wavelength band, the additional image signal (IMAGE 2) may be slowly generated. That is, since the amount of light of the fluorescent material or the amount of light for each wavelength band is small, an additional image sensing unit which is described later should be exposed to the light of the fluorescent material or the light for each wavelength band for a relatively long time, so as to obtain a whole image of the additional image signal (IMAGE 2).

Accordingly, unlike the endoscopy system according to the second embodiment of the present disclosure, if the image signal (IMAGE 1) and the additional image signal (IMAGE 2) are processed through the same path, the processing of the image signal (IMAGE 1) affected such that the image corresponding to the (IMAGE 1) may not be displayed quickly and accurately through the display unit 800.

The endoscopy system according to the second embodiment of the present disclosure may process the image signal (IMAGE 1) and the additional image signal (IMAGE 2) through a different path and may process the image signal (IMAGE 1) at a higher speed in comparison with the additional image signal (IMAGE 2) such that it is possible to quickly and accurately display the image of the inner body.

As shown in FIG. 4 and FIG. 5, the endoscopy system according to the second embodiment of the present disclosure may include a first memory 310 and a second memory 330, and the signal processing unit 200 and the image processing unit 400 may include a direct memory access (DMA) logic respectively to access the first memory 310 and second memory 330 at a high speed.

The direct memory access (DMA) logic of the signal processing unit 200 may dump the image signal (IMAGE 1) and the additional image signal (IMAGE 2) in the first memory 310. In addition, the DMA logic of the image processing unit 400 may read data of the additional image signal (IMAGE 2) or the overlapped user interface and additional image signal (IMAGE 2+User interface) from the second memory 330. In this case, the first memory 310 and the second memory 330 may transmit and receive information on whether to read data through a SYNC communication line.

Meanwhile, the image signal generating unit 100 may include the image sensing unit 120, an additional image sensing unit 140, a serializer 150, and the signal transmission unit 110. In this case, FIG. 4 and FIG. 5 illustrate that the serializer 150 and the signal transmission unit 110 are implemented in a single module, but may be differently implemented in a separate module.

The image sensing unit 120 may generate the image signal (IMAGE 1), and the additional image sensing unit 140 may generate the additional image signal (IMAGE 2). To this end, the image sensing unit 120 may include CCD or CMOS, and the additional image sensing unit 140 may include a sensor or a filter capable of sensing the light of the fluorescent material or the light for each wavelength band.

Figure 6:
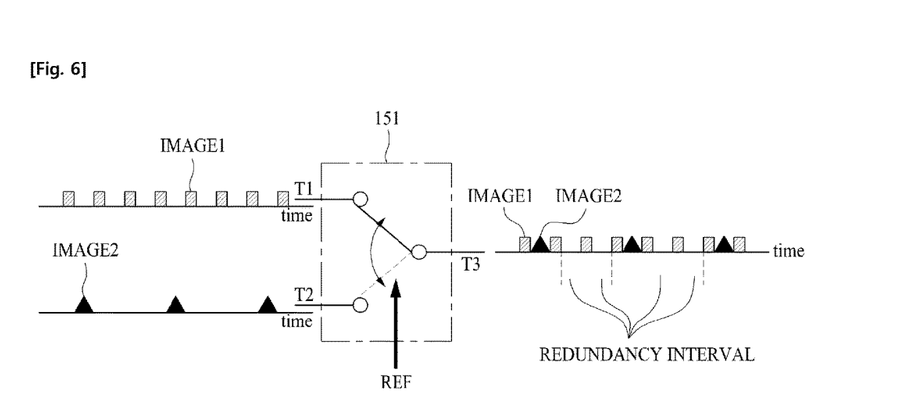
FIG. 6 and FIG. 7 illustrate an operation of a serializer and a deserializer.

The serializer 150 may integrate the image signal (IMAGE 1) and the additional image signal (IMAGE 2) to generate a serial signal. As shown in FIG. 6, the serializer 150 may include a multiplexer (MUX) 151. The MUX 151 may include a first input terminal T1 and a second input terminal T2, and the image signal (IMAGE 1) may be input to the first input terminal T1, and the additional image signal (IMAGE 2) may be input to the second input terminal T2.

At this time, the serializer 150 may switch the first input terminal T1 and the second input terminal T2 according to a reference clock (REF), and may output a serial signal through a single output terminal T3. According to the structure of the serializer 150, the image signal (IMAGE 1) and the additional image signal (IMAGE 2) may be serialized. At this time, the reference clock (REF) may be a transmission band of the serializer 150. For example, the reference clock (REF) may be several Gbps so as to transmit the image signal (IMAGE 1) of Full HD resolution via the serializer 150, but it is not limited thereto.

Due to the structure of the serializer 150, the image signal (IMAGE 1) and the additional image signal (IMAGE 2) does not collide with each other during the formation of a serial signal such that the serial signals may be transmitted without a loss of the image signal (IMAGE 1) and the additional image signal (IMAGE 2).

As shown in FIG. 6, since the data of the additional image signal (IMAGE 2) is small in comparison with the image signal (IMAGE 1), the additional image signal (IMAGE 2) may not be input when a switch is switched to the second input terminal (T2).

Accordingly, since redundancy may be generated in a serialization process of the image signal (IMAGE 1) and the additional image signal (IMAGE 2), the transmission of the serial signal may be stably accomplished in the transmission process.

As the transmission of the serial signal is stably accomplished, the endoscopy system according to the second embodiment of the present disclosure may accurately display the image of the inner body through the display unit 800 when it is used for medical use.

Since the serializer 150 transmits the serial signal without a compression process, a header which is necessary for the compression process is not needed, and a decompression process for the compressed serial signal is also not needed.

Accordingly, the time or the amount of calculation for the compression and the decompression of the serial signal may be reduced, such that it is possible to accomplish a high-speed processing of the image signal (IMAGE 1).

Although the serializer 150 for transmitting the serial signal without compression is described in the above, it is not limited thereto, and the serializer 150 according to the second embodiment of the present disclosure may compress and transmit the serial signal.

Meanwhile, the signal transmission unit 110 may be connected to one side of the cable 500, and may convert and transmit the serial signal into the converted image signal (IMAGE 12') according to the protocol for long distance transmission so as to transmit the serial signal via the cable 500.

FIG. 4 and FIG. 5 illustrate a single image sensing unit 120 and a single additional image sensing unit 140, but it is not limited thereto, and the endoscopy system according to the second embodiment of the present disclosure may include one or more image sensing units 120 and one or more additional image sensing units 140.

The image sensing unit 120 may generate the image signal (IMAGE 1) having n frames per second, and the additional image sensing unit 140 may generate the additional image signal (IMAGE 2) having m frames per second. At this time, m may be smaller than n.

For example, if the additional image signal corresponds to the image of the fluorescent material, it takes time for the additional image sensing unit 140 to collect photon emitted from the fluorescent material. Thus, if the additional image sensing unit 140 generates the additional image signal (IMAGE 2) with 10 frames per second, the image sensing unit 120 may generate the image signal (IMAGE 1) with 60 frames per second.

Meanwhile, as shown in FIG. 4 and FIG. 5, the signal processing unit 200 may include a signal reception unit 210, a deserializer 220, and a path forming unit 230.

The signal reception unit 210 may be connected to the other side of the cable 500, and may receive the converted image signal (IMAGE 12') via the cable 500 to convert into a serial signal.

Figure 7:
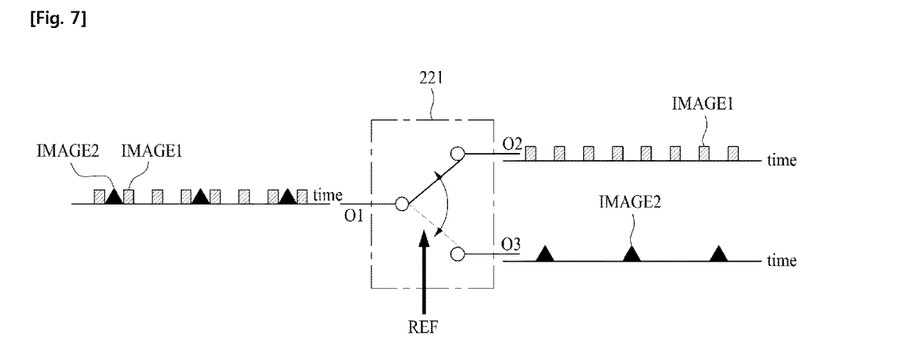

The deserializer 220 may divide the serial signal into the image signal (IMAGE 1) and the additional image signal (IMAGE 2). As shown in FIG. 7, the deserializer 220 may include a demultiplexer (DEMUX) 221.

The DEMUX 221 may include a single input terminals O1, a first output terminal O2, and a second output terminal O3. The serial signal may be input through the input terminal O1. At this time, the deserializer 220 may switch the first output terminal O2 and the second output terminal O3 according to the reference clock (REF).

Accordingly, the image signal (IMAGE 1) may be output to the first output terminal O2, and the additional image signal (IMAGE 2) may be output through another output terminal O3. According to the structure of the deserializer 220, the image signal (IMAGE 1) and the additional image signal (IMAGE 2) may be separated from the serial signal.

At this time, the reference clock (REF) and the point of time of the operation start of the serializer 150 and the deserializer 220 may be identical with each other. Thus, since the serializer 150 and the deserializer 220 are synchronized, the deserializer 220 may divide the serial signal into an original image signal (IMAGE 1) and the additional image signal (IMAGE 2).

The path forming unit 230 may output the image signal (IMAGE 1) to the first transmission path, and output the additional image signal (IMAGE 2) to the second transmission path.

Meanwhile, as shown in FIG. 5, the endoscopy system according to the second embodiment of the present disclosure may further include a monitoring unit 700. The monitoring unit 700 may monitor at least one of the signal processing unit 200, CPU 300, and the image processing unit 400 in real time and may perform at least one reset according to at least one state value.

In addition, the monitoring unit 700 may monitor the serializer 150 and the signal transmission unit 110 in real time and may perform a reset of these elements according to the state value of the serializer 150 and the signal transmission unit 110.

Accordingly, the monitoring unit 700 may perform a rapid and stable display of the image and the additional image of the endoscopy system. Since the monitoring unit 700 is described in the above through the first embodiment, an explanation thereof is omitted.

Meanwhile, the monitoring unit 700 may receive an operation control signal or a processing control signal for controlling the transmission or the conversion of the image signal (IMAGE 1) from CPU 300, and may transmit a control command corresponding to the operation control signal or the processing control signal to at least one of the signal transmission unit 110, the signal processing unit 200, and the image processing unit 400.

At this time, since the operation control signal and the processing control signal are described in the above in detail through the first embodiment, detail description thereof is omitted.

Meanwhile, as described above, for the smooth progress of the surgery or the checkup, the image signal (IMAGE 1) should be processed as fast as possible, and the time for generating the additional image signal (IMAGE 2) of one frame may be long in comparison with the image signal (IMAGE 1).

Therefore, the transmission speed of the image signal (IMAGE 1) in the first transmission path may be faster than the transmission speed of the additional image signal (IMAGE 2) in the second transmission path, and the bandwidth of the image signal (IMAGE 1) in the first transmission path may be wider than the bandwidth of the additional image signal (IMAGE 2) in the second transmission path.

In addition, when CPU 300 performs an image processing of the image signal (IMAGE 1), the image processing speed of the image signal (IMAGE 1) by the image processing unit 400 may be faster than the image processing speed by CPU 300.

For example, CPU 300 may match the image signal (IMAGE 1) with a disease display image data of the database or the local table, and the matching result may be overlapped on the image signal (IMAGE 1) processed by the image processing unit 400.

Since this is described in detail in the above through the first embodiment, a description thereof is omitted.

Meanwhile, CPU 300 may output a processing control signal for selecting at least one of the plurality of filters of the image processing unit 400. The filter selected according to the processing control signal may process at least one of the image signal (IMAGE 1) and the additional image signal (IMAGE 2) at a high-speed in comparison with the image processing speed of CPU 300.

The operation control signal of CPU 300 may be a signal corresponding to the user interface, or may be a signal for controlling a hardware such as the light emitting unit 130.

As mentioned in the above, the endoscopy system according to the second embodiment of the present disclosure may process the image signal (IMAGE 1) and the additional image signal (IMAGE 2) through a separate path such that the image signal (IMAGE 1) may be processed at a high speed.

Accordingly, in the case of the endoscopy system according to the second embodiment of the present disclosure, a time taken from a generation of the image signal (IMAGE 1) to a display of the image signal (IMAGE 1) through the display unit 800 may be within 100 ms, preferably, within 30 ms. If the time is within 30 ms, the doctor using the endoscopy system may hardly feel the time delay visually.

In addition, a time taken from a generation of the additional image signal (IMAGE 2) by the additional image sensing unit 140 to a display of the additional image signal (IMAGE 2) may 100 ms to 500 ms, which may be longer than the time of the image signal (IMAGE 1).

Meanwhile, CPU 300 may output an integrated image (IMAGE 2+User interface) integrating the additional image signal (IMAGE 2) and the user interface to the image processing unit 400, and the image processing unit 400 may overlap the integrated image (IMAGE 2+User interface) and the image signal (IMAGE 1).

Unlike the second embodiment of the present disclosure, when the image processing unit 400 overlaps the additional image signal (IMAGE 2) and the user interface with the image signal (IMAGE 1) respectively, the amount of calculation for overlapping may be increased in the image processing unit 400.

On the other hand, as in the second embodiment of the present disclosure, when the image processing unit 400 may overlap the integrated image (IMAGE 2+User interface) and the image signal (IMAGE 1) after CPU 300 generates the integrated image (IMAGE 2+User interface), the amount of calculation may be reduced.

The endoscopy system according to the second embodiment of the present disclosure may further include the light emitting unit 130 for irradiating light to the inner body. In this case, when the amount of the radiated light exceeds the amount of light that can be accepted by the image sensing unit 120, CPU 300 may control the light emitting unit 130 to reduce an intensity of the light.

For example, if the light amount is unacceptable and the image sensors of the image sensing unit 120 are saturated, the image signal may continue to output a FFFF signal representing the saturation. When it exceeds a certain area of the entire area of the image sensor, CPU 300 may determine that the light is excessively intense and may output the operation control signal for reducing the amount of light to the light emitting unit 130.

The image signal generating unit 100 may further include a first conversion unit 160 which converts a converted image signal (IMAGE 12') into an analog signal to transmit to one side of the cable 500. In addition, the signal processing unit 200 may further include a second conversion unit 240 which converts the analog signal transmitted via the other side of the cable 500 into a converted image signal (IMAGE 12') of a digital signal type.

The first conversion unit 160 may include a phy chip connected to one side of the cable 500, and the second conversion unit 240 may include a dephy chip connected to the other side of the cable 500.

The pie chip may convert the converted image signal (IMAGE 12') of a digital signal type into an analog signal, and the dephy chip may convert the analog signal into a converted image signal (IMAGE 12') of a digital signal type.

Unlike the second embodiment of the present disclosure, when a square wave digital signal cable 500 is transmitted to a distance at a high-speed of several Gbps to the signal processing unit 200 via the cable 500, an edge of the square wave may be distorted. To prevent this, the endoscopy system according to the second embodiment of the present disclosure may convert the converted image signal (IMAGE 12') of a digital signal type into an analog signal so that it is possible to transmit the converted image signal (IMAGE 12') to a distance at a high-speed.

Meanwhile, the cable 500 of the endoscopy system according to the first embodiment and the second embodiment of the present disclosure may be a coaxial cable or a twisted cable. The coaxial cable or the twisted cable may reduce or prevent electromagnetic wave effects.

As explained above, since the serial signal of several Gbps may be transmitted through the cable 500, the coaxial cable or the twisted cable may reduce the effect of electromagnetic waves. Accordingly, the endoscopy system according to the first embodiment and the second embodiment of the present disclosure may cope with a task which requires a high degree of safety such as a surgery or a checkup.

CPU 300 may output the user interface for at least one of the image signal (IMAGE 1) and the additional image signal (IMAGE 2) and the operation control signal according to the handling of the user interface of a user.

The image processing unit 400 may overlap the user interface together with the image signal (IMAGE 1) and the additional image signal (IMAGE 2) and may process the at least one of the image signal (IMAGE 1) and the additional image signal (IMAGE 2) according to the operation control signal.

As shown in FIG. 2 to FIG. 4, CPU 300 of the endoscopy system according to the first embodiment and the second embodiment of the present disclosure may access a hospital network such as a PACS server and may transmit and receive data.

Accordingly, since the endoscopy system according to the first embodiment and the second embodiment of the present disclosure may store the image signal, the additional image signal, and the user interface in a server of the hospital network, a separate digital image recorder (DVR) may not be necessary.

Since the input unit 750 and the video port 600 of FIG. 3 and FIG. 4 are described in detail through the first embodiment, an explanation thereof is omitted.

Figure 8:
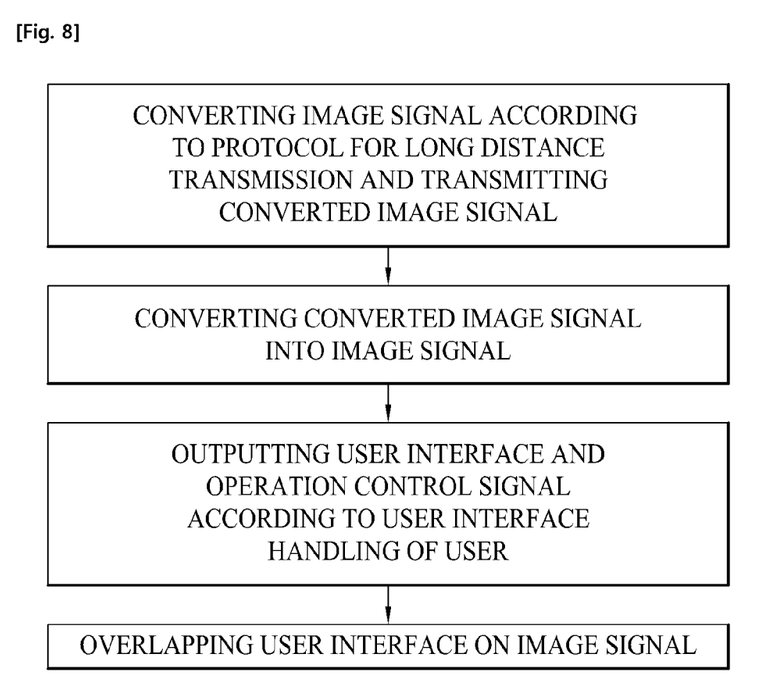
FIG. 8 and FIG. 9 illustrate a flowchart of an image processing method of an endoscopy system according to a third embodiment and a fourth embodiment of the present disclosure.
Figure 9:
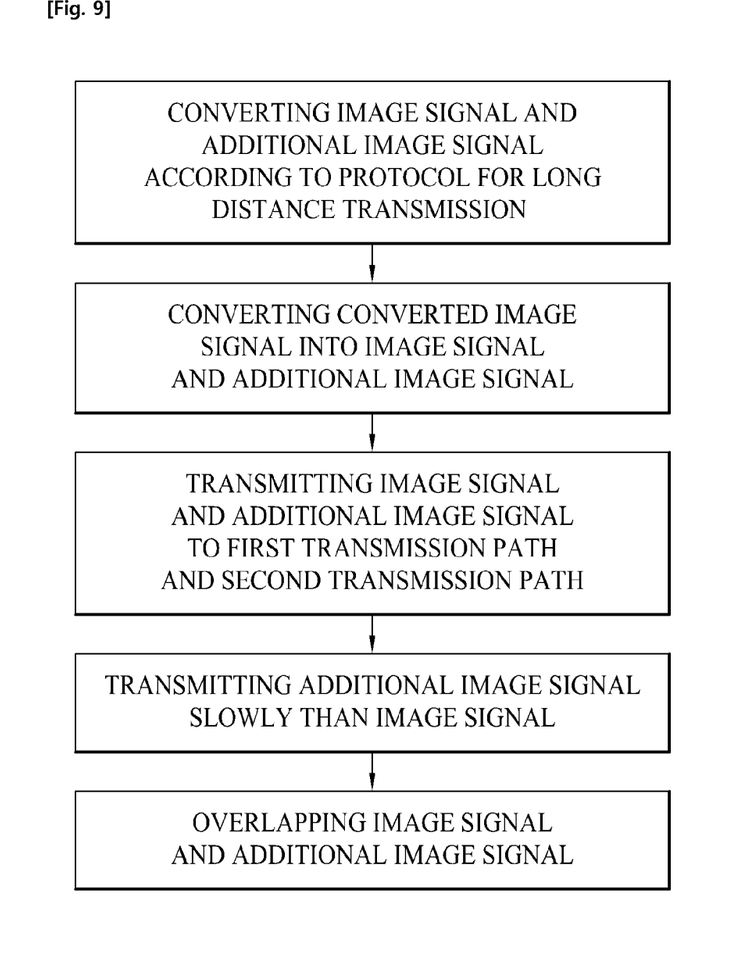

FIG. 8 and FIG. 9 illustrate a flowchart of an image processing method of an endoscopy system according to a third embodiment and a fourth embodiment of the present disclosure.

As shown in FIG. 8, the image processing method of the endoscopy system according to a third embodiment of the present disclosure may include a step of converting the image signal (IMAGE 1) according to a protocol for long distance transmission and transmitting a converted image signal (IMAGE 1') so as to achieve the transmission of the image signal (IMAGE 1) of the inner body through the cable 500 of an endoscope, a step of receiving the converted image signal (IMAGE 1') transmitted through the cable 500 and converting the converted image signal (IMAGE 1') into the image signal (IMAGE 1), a step of outputting the user interface for the image signal (IMAGE 1) and the operation control signal according to the handling of the user interface by a user, and a step of overlapping the user interface on the image signal (IMAGE 1) and processing the image signal (IMAGE 1) according to the operation control signal.

Since the above operation is mentioned in detail through the endoscopy system according to the first embodiment of the present disclosure, a description thereof is omitted.

Meanwhile, as shown in FIG. 9, the image processing method of the endoscopy system according to a fourth embodiment of the present disclosure may include a step of converting an image signal (IMAGE 1) of inner body having n frames per second and an additional image signal (IMAGE 2) of inner body having m frames per second into a converted image signal (IMAGE 12') according to the protocol for long distance transmission so that it is possible to transmit the image signal (IMAGE 1) and the additional image signal (IMAGE 2) via the cable 500, a step of converting the converted image signal (IMAGE 12') transmitted through the cable 500 into the image signal (IMAGE 1) and the additional image signal (IMAGE 2), and transmitting the image signal (IMAGE 1) and the additional image signal (IMAGE 2) to a first transmission path and a second transmission path, a step of transmitting the additional image signal (IMAGE 2) transmitted through the second transmission path at a speed slower than the transmission speed of the image signal (IMAGE 1) in the first transmission path, and a step of overlapping the image signal (IMAGE 1) transmitted through the first transmission path and the additional image signal (IMAGE 2) output from CPU.

Since the above operation is mentioned in detail through the endoscopy system according to the second embodiment of the present disclosure, a description thereof is omitted.

The endoscopy system and the method for processing an image of the endoscopy system according to an embodiment of the present disclosure is capable of performing a high speed image processing and providing various functions by implementing a different processing path of the image signal and the user interface.

The endoscopy system and the method for processing an image of the endoscopy system according to an embodiment of the present disclosure is capable of performing a high-speed processing of an image signal by processing the image signal and the additional image signal through a different path.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An endoscopy system comprising:
    an image signal generating unit which is connected to one side of a cable, and which is configured to convert an image signal of inner body having n frames per second and an additional image signal of inner body having m frames per second into a converted image signal according to a protocol for long distance transmission so that it is possible to transmit the image signal and the additional image signal via the cable;

a signal processing unit which is connected to the other side of the cable, and which is configured to convert the converted image signal transmitted through the cable into the image signal and the additional image signal, and to transmit the image signal and the additional image signal to a first transmission path and a second transmission path respectively;

a CPU configured to transmit the additional image signal transmitted via the second transmission path at a speed lower than a transmission speed of the image signal in the first transmission path; and an image processing unit configured to overlap the image signal transmitted through the first transmission path and the additional image signal output from the CPU.

2. The endoscopy system of claim 1, wherein the image signal generating unit comprises:

an image sensing unit configured to generate the image signal;

an additional image sensing unit configured to generate the additional image signal;

a serializer configured to integrate the image signal and the additional image signal to generate a serial signal; and a signal transmission unit which is connected to one side of the cable, and which is configured to convert and transmit the serial signal into the converted image signal according to the protocol for long distance transmission so as to transmit the serial signal via the cable.

3. The endoscopy system of claim 2, wherein the signal processing unit comprises:

a signal reception unit which is connected to the other side of the cable, and which is configured to receive the converted image signal via the cable to convert into the serial signal;

a deserializer configured to divide the serial signal into the image signal and the additional image signal; and a path forming unit configured to output the image signal to the first transmission path, and output the additional image signal to the second transmission path.

4. The endoscopy system of claim 1, further comprising a monitoring unit that monitors at least one of the signal processing unit, the CPU, and the image processing unit in real time to perform at least one reset according to at least one state value.

5. The endoscopy system of claim 1, wherein a transmission speed of the image signal in the first transmission path is faster than a transmission speed of the additional image signal in the second transmission path.

6. The endoscopy system of claim 1, wherein a bandwidth of the image signal in the first transmission path is wider than a bandwidth of the additional image signal in the second transmission path.

7. The endoscopy system of claim 1, wherein, when the CPU performs an image processing for the image signal, an image processing speed for the image signal by the image processing unit is faster than the image processing speed by the CPU.

8. The endoscopy system of claim 1, further comprising a light emitting unit that irradiates a light to the inner body, wherein the image signal generating unit comprises an image sensing unit that generates the image signal, and, when an amount of the radiated light exceeds an amount of light that can be accepted by the image sensing unit, the CPU controls the light emitting unit to reduce an intensity of light.

9. The endoscopy system of claim 1, wherein the image signal generating unit further comprises a first conversion unit that converts the converted image signal into an analog signal to transmit to one side of the cable, and the signal processing unit further comprises a second conversion unit that converts the analog signal transmitted via the other side of the cable into the converted image signal of a digital signal type.

10. The endoscopy system of claim 1, wherein the cable is a coaxial cable or a twisted cable.

11. The endoscopy system of claim 1, wherein the CPU outputs a user interface for at least one of the image signal and the additional image signal, and outputs an operation control signal according to a user interface handling of a user, and the image processing unit overlaps the user interface together with the image signal and the additional image signal and processes at least one of the image signal and the additional image signal according to the operation control signal.

12. The endoscopy system of claim 4, wherein the monitoring unit receives an operation control signal or a processing control signal for controlling transmission or conversion of the image signal from the CPU, and transmits a control command corresponding to the operation control signal or the processing control signal to at least one of the signal transmission unit, the signal processing unit, and the image processing unit.

13. The endoscopy system of claim 2, wherein the image sensing unit generates the image signal of n frames per second, the additional image sensor generates the additional image signal of m frames per second, and the m is smaller than the n.

* * * * *